(12) United States Patent
Shah (10) Patent No.: US 6,352,077 B1
(45) Date of Patent: Mar. 5, 2002

(54) FILM WELDED RESERVOIR BAG FOR BREATHING CIRCUIT AND METHOD OF MAKING THE SAME

(76) Inventor: Tilak M. Shah, 104 Lochberry La., Cary, NC (US) 27511

( * ) Notice: Subject to any disclaimer, the term of this patent is extended or adjusted under 35 U.S.C. 154(b) by 0 days.

(21) Appl. No.: 09/562,334

(22) Filed: May 1, 2000

(51) Int. Cl.⁷ .................................................. A62B 7/00
(52) U.S. Cl. ............................ 128/205.17; 128/205.13
(58) Field of Search ..................... 128/205.13, 205.17, 128/204.18, 204.28, 910, DIG. 24, 200.22, 202.28, 203.12, 203.28; 264/322, 248, 491; 156/272.2, 274.4

(56) References Cited

U.S. PATENT DOCUMENTS

| | | | | |
|---|---|---|---|---|
| 2,818,861 A | * | 1/1958 | Russell | 128/205 |
| 3,045,672 A | * | 7/1962 | Croasdaile | 128/205 |
| 3,473,529 A | * | 10/1969 | Wallace | 128/145.7 |
| 3,773,045 A | * | 11/1973 | Boba | 128/202 |
| 3,859,997 A | * | 1/1975 | Douma et al. | 128/188 |
| 4,263,236 A | * | 4/1981 | Briggs et al. | 264/26 |
| RE31,671 E | * | 9/1984 | Bonk et al. | 528/65 |
| 5,403,123 A | * | 4/1995 | Walters | 405/286 |
| 5,408,995 A | * | 4/1995 | Contino et al. | 128/205.25 |
| 5,469,863 A | | 11/1995 | Shah | 128/844 |
| 5,599,219 A | * | 2/1997 | Green | 441/106 |
| 5,679,423 A | | 10/1997 | Shah | 428/35.2 |
| 5,693,412 A | * | 12/1997 | Walters | 428/317.1 |
| 5,795,211 A | * | 8/1998 | Carignan et al. | 446/220 |
| 5,833,915 A | | 11/1998 | Shah | 264/491 |
| RE35,991 E | * | 12/1998 | Desmarais et al. | 156/274.4 |
| 5,862,916 A | * | 1/1999 | Utecht | 206/570 |
| 6,054,525 A | * | 4/2000 | Schloman, Jr. et al. | 524/575.5 |
| 6,189,744 B1 | * | 2/2001 | Rince | 222/386.5 |
| 6,250,047 B1 | * | 6/2001 | Ahern et al. | 53/430 |

* cited by examiner

Primary Examiner—John G. Weiss
Assistant Examiner—Teena Mitchell
(74) Attorney, Agent, or Firm—Steven J. Hultquist; Marianne Fuierer (57) ABSTRACT

A pulmonarily sized bag formed of a non-latex material, including a bag body formed of panels of resin film material welded to one another along a weld line defining a seam of the bag body bounding an interior volume of the bag. The seam includes an interior seam portion in the interior volume, and an exterior seam portion at an exterior surface of the bag. One of the interior seam portion and exterior seam portion comprises free edges of the seam, and the other one of such seam portions is devoid of free edges. The bag is formable by various techniques, including radio frequency welding, impulse heating, solvent bonding, etc., and is usefully employed in a breathing circuit to obviate the necessity of using latex breathing bags.

29 Claims, 4 Drawing Sheets

FILM WELDED RESERVOIR BAG FOR BREATHING CIRCUIT AND METHOD OF MAKING THE SAME

BACKGROUND OF THE INVENTION

1. Field Of The Invention

The present invention relates to film welded reservoir bags with seam structure, of a type useful in breathing circuits, and to a novel method of making such reservoir bags.

2. Description of the Related Art

Breathing circuits are commonly used for anesthesia administration, pulmonary treatments such as administration of lung surfactants to neonatal patients, delivery of therapeutic agents such as pentamidine to the alveoli of the lungs, etc., and oxygen administration.

Such breathing circuits typically incorporate a gas source or other supply for the medicament or treatment agent, e.g., a nebulizer or entrainment device for introducing the therapeutic agent into a gas stream for delivery to the patient, together with waste gas or contaminant removal means such as chemisorbents (scavengers) or physical adsorbents, which may for example remove $CO_2$ from the breathing circuit. A mask or intubating conduit may be utilized in the circuit for delivery of the treatment gas to the patient.

The breathing circuit also variously includes reservoir bags, sometimes termed ventilator bags. The function of such bags is to provide a hold-up or expansion volume that may be selectively (manually or automatically) compressed to cause flow of the treatment gas to the patient.

Conventional reservoir bags are formed of latex and available in differing sizes (e.g., 1, 2 and 3 liter volumes). Conductive latex is frequently used in circumstances where the treatment gases are flammable in character.

Latex bags of such type are formed by dip-molding processes, in which a mandrel is dipped into a latex bath to coat the mandrel with a thin film of the latex material, followed by drying and curing of the latex and removal of the bag article from the mandrel. Such latex bags are seamless in character.

Although latex reservoir bags are readily produced in large volume at relatively low cost, they suffer the disadvantage, common to latex generally, that a significant portion of the population experiences allergic or antigenic reactions in exposure to latex. For this reason, it is desirable to provide a reservoir bag of non-latex construction, to obviate the risk and danger associated with latex.

Non-latex breathing bags are known, however, all of such bags are made by dip-molding processes and are seamless, which means that such materials must have an elongation of at least 1000% to accommodate demolding (removal) from the mandrel on which the bag is formed.

Unfortunately, there exist few non-latex materials that have elongation in excess of 1000% and are suitable for dip-molding. Such materials include synthetic latex materials, polyisoprene, nitrile rubbers and silicones, but such materials are relatively expensive in relation to latex and/or have other deficiencies that have limited their commercial use for reservoir bag fabrication.

SUMMARY OF THE INVENTION

The present invention relates to a bag with seam formed by welding of two layers of film of non-latex material and having application as a breathing circuit component.

In one aspect, the invention relates to a pulmonarily sized bag formed of a non-latex material, comprising a bag body formed of panels of resin film material welded to one another along a weld line defining a seam of the bag body bounding an interior volume of the bag, wherein the seam comprises an interior seam portion in the interior volume, and an exterior seam portion at an exterior surface of the bag, and wherein one of the interior seam portion and exterior seam portion comprises free edges of the seam, and wherein the other of the interior seam portion and the exterior seam portion at the exterior surface of the bag is devoid of free edges.

In another aspect, the invention relates to a method of forming a pulmonarily sized bag, comprising superpositioning sheets of a non-latex material on one another, welding the superpositioned sheets to one another along a weld line defining the shape of the bag and forming a seam comprising free seam edges, thereby producing a welded article.

Other aspects, features and embodiments of the invention will be more fully apparent from the ensuing disclosure and appended claims.

DETAILED DESCRIPTION OF THE INVENTION AND PREFERRED EMBODIMENTS THEREOF

The bag of the present invention is formed of a non-latex material, by a heat-sealing process, using thin film material in which superposed layers of the film material are heat-sealed to one another, to form a bag body including an interior volume bounded by a heat-sealed seam.

The bag may be used in such conformation, and optionally a collar may be attached to a neck portion of the bag. Such collar attachment may be effected as a post-formation operation, after the bag body has been formed by heat-sealing of the constituent sheets of film material.

Alternatively, a collar element may be formed in situ in the seam-bonding operation. In such alternative formation method, a collar element is placed at a neck region of the bag to be formed, following by heat-sealing the respective sheets around the collar external surface. By this technique, the respective film sheets are bonded to the collar element and to one another at the neck region of the bag. The collar may have a flanged lip, or be threaded, or alternatively be formed to facilitate coupling to the breathing circuit in which the bag is deployed.

The bag may be formed so that the heat-sealing of the seam produces an exterior seam on the bag. In such construction, it is desirable to form the seam in such manner as to minimize the formation of excess "free edge" material at the seam. This minimum seam condition can be carried out with post-heat-sealing trimming of the "flash" excess edge material, but it is generally desirable to avoid such step if possible, by conducting the heat-sealing operation so that excess free edge material is not formed.

The bag as formed may in an optional further aspect be subjected to an inversion operation, i.e., be turned inside out after the heat-sealing operation, to yield the bag with interiorly extended seam edges, and a smooth exterior in the vicinity of the seam.

The bag is pulmonarily sized, i.e., sized for use in a breathing circuit with a volume correlative to the pulmonary volume of a patient, in a range of from about 0.5 liters to about 5 liters. More preferably, the interior volume of the bag is in the range of from about 0.75 to about 4 liters, and most preferably such interior volume of the bag is from about 1 to about 3 liters.

The bag is formed of a resin film material, and has a low modulus, rubbery "hand" character, as suitable for breathing circuit deployment. The modulus (here meaning the modulus of elasticity at 50% elongation), is suitably below about 1500 pounds per square inch (psi), preferably being in the range of from about 50 to about 800 psi, and most preferably in the range of from about 50 to about 500 psi.

Such modulus characteristics permit the bag to satisfy pressure/burst test requirements, according to which the introduction of 2–3 times the design air volume into the bag must not cause the pressure of gas in the bag to exceed a predetermined pressure limit, so that the bag must expand or burst under such volumetric loading test.

The durometer value of the resin film material is suitably below 98 A, being advantageously in the range of from about 90 to about 10 A, more preferably in the range of from about 20 to about 85 A, and most preferably from about 30 A to about 75 A.

Among resin film materials useful in the broad practice of the present invention, illustrative materials include: polyurethane having a durometer not exceeding about 90 A; styrene-isoprene-styrene/styrene-butadiene-styrene compositions, such as Kraton® polymers (commercially available from Shell Chemical Company, Houston, Tex.); polyvinylchloride (PVC) that has been plasticized to the desired flexibility and hand characteristics; urethane/PVC blends; urethane that has been plasticized to the desired flexibility and hand characteristics; Covale™ polymer (commercially available from Dow Chemical Company, Midland, Mich.); polyester elastomers such as Hytrel® (commercially available from E.I. DuPont de Nemours & Company, Wilmington, Del.); polyamide elastomers such as Pebax® (commercially available from Atochem); olefinic polymers (polypropylene, polyethylene, etc.); and metallocene polymers.

A preferred resin film material is polyurethane film having a durometer not exceeding about 90 A.

The resin film material used to fabricate the bag may be used in the form of a blown film, extruded sheet, solvent cast film or other suitable web stock formed of the resin material.

Thickness of the bag wall and the constituent sheets of resin film material used to form the bag, is typically in the range of from about 1 to about 25 mils, more preferably in the range of from about 2 to about 10 mils, and most preferably in the range of from about 2 to about 6 mils.

The finish of the resin film sheets used to fabricate the bag is preferably a matte finish on the surface that ultimately will comprise the exterior surface of the bag. The sheets may have a smooth (gloss) finish on the opposite side, i.e., the side that ultimately will comprise the interior surface of the bag, or both ultimately exterior and ultimately interior surfaces may have a matte finish.

An exterior surface matte finish is desired to ensure grippability of the bag in use, by a doctor, nurse or medical technician engaged in manual compression or decompression of the bag, or by automated compression/expansion control means. The matte finish may be imparted to the resin film sheet by embossed roller or rubber roller processing, chemical etching, mechanical abrasion, or any other suitable techniques.

The resin film sheets from which the bag is fabricated can contain dye or pigment additives to impart a desired color to the bag, and the resins from which the sheets are formed may be blended with other additives, such as tackifiers, antioxidants, uv stabilizers, dispersing agents, fillers, surfactants, surface modifiers, heat stabilizers, flame retardants, etc., as necessary or desirable to the end use of the bag. The sheet stock used to fabricate the bag can also contain conductive material, e.g., carbon black or metallic particulate materials, to impart conductivity characteristics to the bag rendering it suitable for use in anaesthesia breathing circuits employing flammable gases.

The resin film sheets are fabricated into the product bag article by heat-sealing superposed sheets to form a heat seal seam with free seam edges, on the exterior surface of the bag if the bag is used in the originally formed conformation. Alternatively, the heat seal seam free edges may be disposed in the interior volume of the bag if the bag subsequent to heat sealing is inverted, so that the seam is smooth on the exterior surface of the inverted bag.

In either case, it is desirable to minimize the amount of free edge material, e.g., protuberant flanges or "flash" material at the heat-sealed seam, and this is accommodated by the process variations described hereinafter.

In one such process variation, radio frequency welding is employed to heat-seal the edge seam of the bag formed by superposed sheets of the resin film.

By way of example, for the aforementioned preferred polyurethane film having a 70 A durometer hardness, radio frequency (RF) welding of the edge seams of the superposed sheets can be carried out at a temperature of from about 100° F. to about 300° F., most preferably at a temperature in the vicinity of 250° F. The corresponding RF power level is in the range of from about 100 to about 500 milliamps, most preferably in the vicinity of 400 milliamps. A cycle time for the RF welding operation may be of corresponding duration as necessary to achieve continuous seam welding of the superposed sheets at the seam regions of the sheets.

In one embodiment, a cycle time of 15 seconds of RF welding comprises the following cycle steps:

| | |
|---|---|
| Preheating | 1.5 seconds |
| RF welding | 2.5 seconds |
| Cooling | 1.0 second |
| Open/close | 10 seconds |

As another variant sheet joining technique, seam joining of the sheets can also be carried out by impulse heating of the superposed resin film sheets, at a temperature of from about 300° F. to about 500° F. for a time of from about 3 to about 10 seconds.

As a still further sheet joining technique, adhesive or solvent bonding of the superposed sheets can be carried out, using suitable adhesive formulation or solvent medium. By way of example, solvent bonding of the preferred material polyurethane sheets can be carried out by solvent bonding using tetrahydrofuran (THF) as the solvent bonding medium, or such polyurethane sheets can be adhesively bonded by a THF/polyurethane blend adhesive composition.

The seam itself must be continuous along the joined sheets so that air, anaesthesia gases or other fluid medium in the bag is leak-tightly contained in the interior volume of the bag when in use. The bag desirably has a minimum seam dimension between the joined sheets that is at least twice the thickness of the sheet stock used in the bag. Sheets used in the bag desirably have a same thickness relative to one another, so that the bag is substantially uniform in thickness and physical/performance properties with respect to the component sheets making up the bag. The bag desirably has a maximum seam dimension between the joined sheets that is about 0.5 inch.

Preferred seam characteristics include a seam dimension that is in the range of from about 0.020 to about 0.050 inch in bags formed by inversion of the bag body subsequent to seam-joining of the component sheets of resin film material. For seams of bags that are not inverted subsequent to seam-joining of the component sheets, seam dimensions in the range of from 0.050 to about 0.125 inch are satisfactory. If the bag body formed by seam-joining of superposed sheets of resin film material is not inverted, it generally is desirable to achieve very good control of the seam-forming and any associated free edge trimming steps, to produce an aesthetic appearance in the product bag article.

In preferred practice, the seam strength of the bag should be at least about 1000 pounds per square inch (psi), or alternatively at least about 30% of the strength of the unwelded film.

For impulse heat welding as the welding method used to join the superposed sheets of resin film material, the seam dimension is suitably at least twice the thickness of the film stock used in the bag, and preferably the seam dimension does not exceed about 0.5 inch. Preferred seam characteristics of heat impulse-welded bags include a seam dimension that is in the range of from about 0.020 to about 0.050 inch in bags formed by inversion of the bag body subsequent to seam-joining of the component sheets of resin film material. For seams of heat impulse-welded bags that are not inverted subsequent to seam-joining of the component sheets, seam dimensions in the range of from 0.050 to about 0.125 inch are satisfactory.

The shape of the bag may include any suitable conformation or form, e.g., circular, oval, dumbbell, S-shape, etc.

Figure 1:
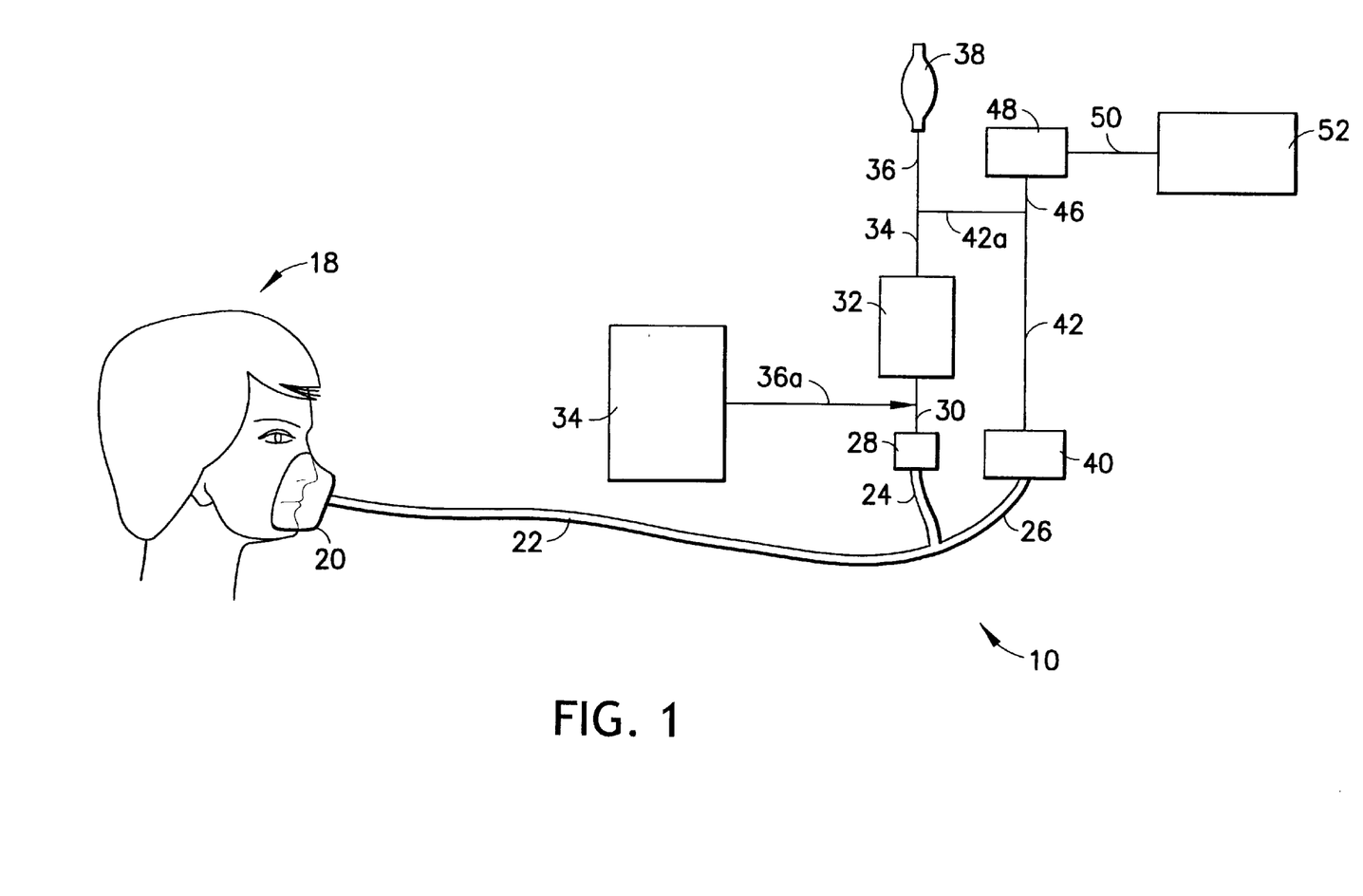
FIG. 1 is a schematic representation of a bag according to one embodiment of the invention as a component of a breathing circuit.

Referring now to the drawings, FIG. 1 is a schematic representation of a bag 38 according to one embodiment of the invention as a component of a breathing circuit 10.

The breathing circuit 10 includes a mask 20 delivering anaesthesia gases to a patient 18. Mask 20 is joined to a delivery/discharge conduit 22 having branch lines 24 and 26 joined to the respective one-way valves 28 and 40. Branch line 24 is an inspiration line and branch line 26 is an expiration line.

The reservoir bag 38 is joined to bi-directional flow line 36, which in turn is joined to lines 42a and 34, as shown. Line 34 is coupled with $CO_2$ absorber 32, which is coupled in turn to line 30 connected to the one-way valve 28.

Anaesthesia gases are supplied by anaesthesia machine 34, via supply line 36a, and flow to line 30 of the breathing circuit, for flow through line 30, one-way valve 28, branch line 24, and delivery/discharge conduit 22 to the patient.

The breathing circuit contains an adjustable pressure-limiting valve 48, joined by line 50 to the scavenging unit 52, which removes undesired gas from the recirculated gases flowing from the patient through delivery/discharge conduit 22, branch line 26, one-way valve 40 and recirculation line 42. Specifically, a portion of the flow from the recirculation line 42 when the pressure builds to a level above the set point of the adjustable pressure-limiting valve 48 flows in discharge line 46 through the adjustable pressure-limiting valve 48 and line 50 to the scavenging unit 52.

In the operation of the FIG. 1 system, the breathing bag 38 fills with gas from the breathing circuit and the bag may be manually or automatically compressed to effect flow of gas to the patient in a manner consistent with the patient's pulmonary volume and respiratory function.

Figure 2A:
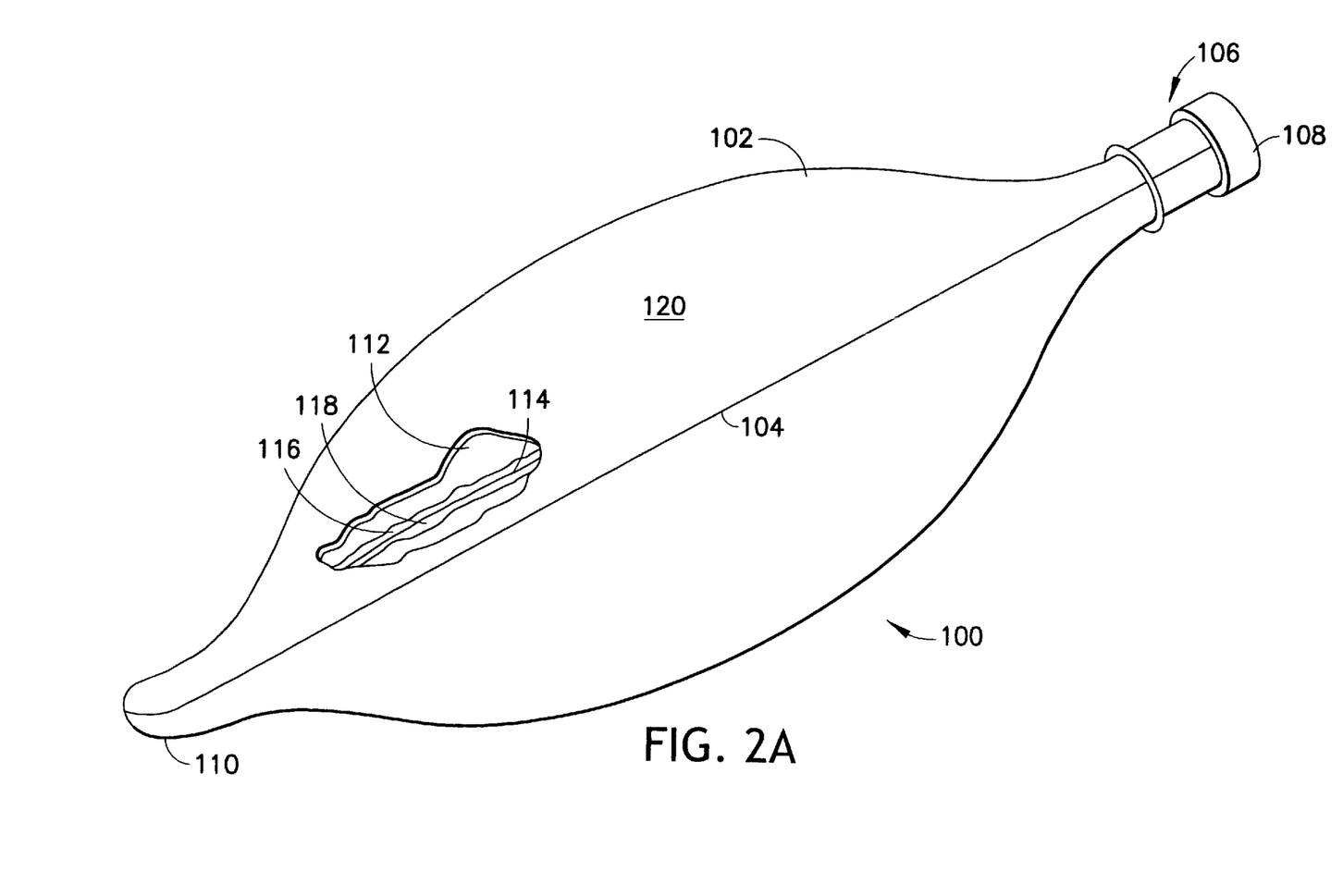
FIG. 2A is a perspective view of a bag according to one embodiment of the invention.

FIG. 2A is a perspective view of a bag 100 according to one embodiment of the invention. The bag 100 comprises a bag body 102 formed from two sheets of resin film material welded at a seam 104, and having an exterior surface 120 that optionally features a matte finish to facilitate handling and manual manipulation of the bag.

The bag 100 is formed with a neck 106 including a collar 108 for attachment to the breathing circuit or other coupling or fixturing means. As shown, the bag has an elongate character, with an enlarged intermediate section tapering to the neck 106, as well as tapering to the distal end 110. The bag encloses an interior volume 112 which can be of a volume in the range of 1 to 3 liters.

The seam 104 is continuous about the perimeter of the respective sheets forming the bag and the seam comprises seam edges 116 and 118 bounding the weld 114 of the seam as shown in the breakaway portion of the bag in FIG. 2A. The seam edges are the free ends of the constituent resin film material sheets that were welded to form the seam structure. These free ends thus protrude from the weld 114, and are desirably as small as possible to avoid wastage of sheet material in the forming process for the bag. The free ends may optionally be trimmed to minimize their dimensional character (outwardly extending from the weld) but such trimming is preferably avoided to minimize the risk of damage to the seam itself.

The bag shown in FIG. 2A thus has an interior welded structure that has been interiorly disposed by inversion of the bag article as originally formed by welding. In this manner, the free edge structure associated with the seam is disposed in the interior volume of the bag, so that the outer surface 120 exhibits a smooth seam 104 on such surface, to enhance the aesthetic character of the bag, and improve its functional character (e.g., handleability, resistance to damage to the seam structure by virtue of the interiorly disposed free ends of the constituent sheets, etc.).

Figure 2B:
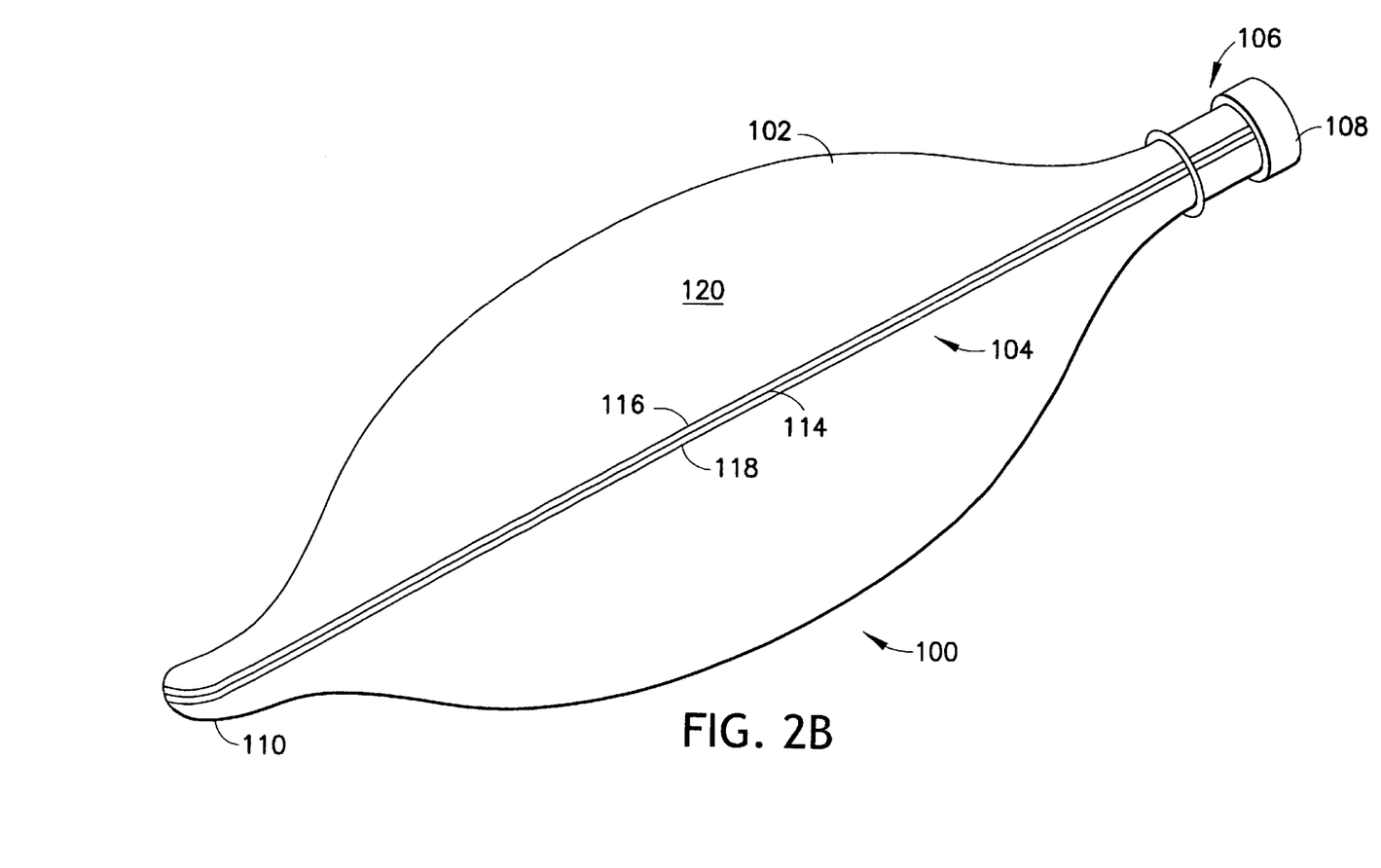
FIG. 2B is a perspective view of a bag according to another embodiment of the invention.

FIG. 2B is a perspective view of a bag according to another embodiment of the invention, in which all parts and features of the bag that correspond to those of the FIG. 2A embodiment being correspondingly numbered for ease of reference.

As shown in FIG. 2B, the seam 104 is continuous about the perimeter of the respective sheets forming the bag and the seam comprises seam edges 116 and 118 bounding the weld 114 of the seam as shown on the exterior of the bag in FIG. 2B. The seam edges are the free ends of the constituent resin film material sheets that were welded to form the seam structure. These free ends thus protrude from the weld 114.

Figure 3:
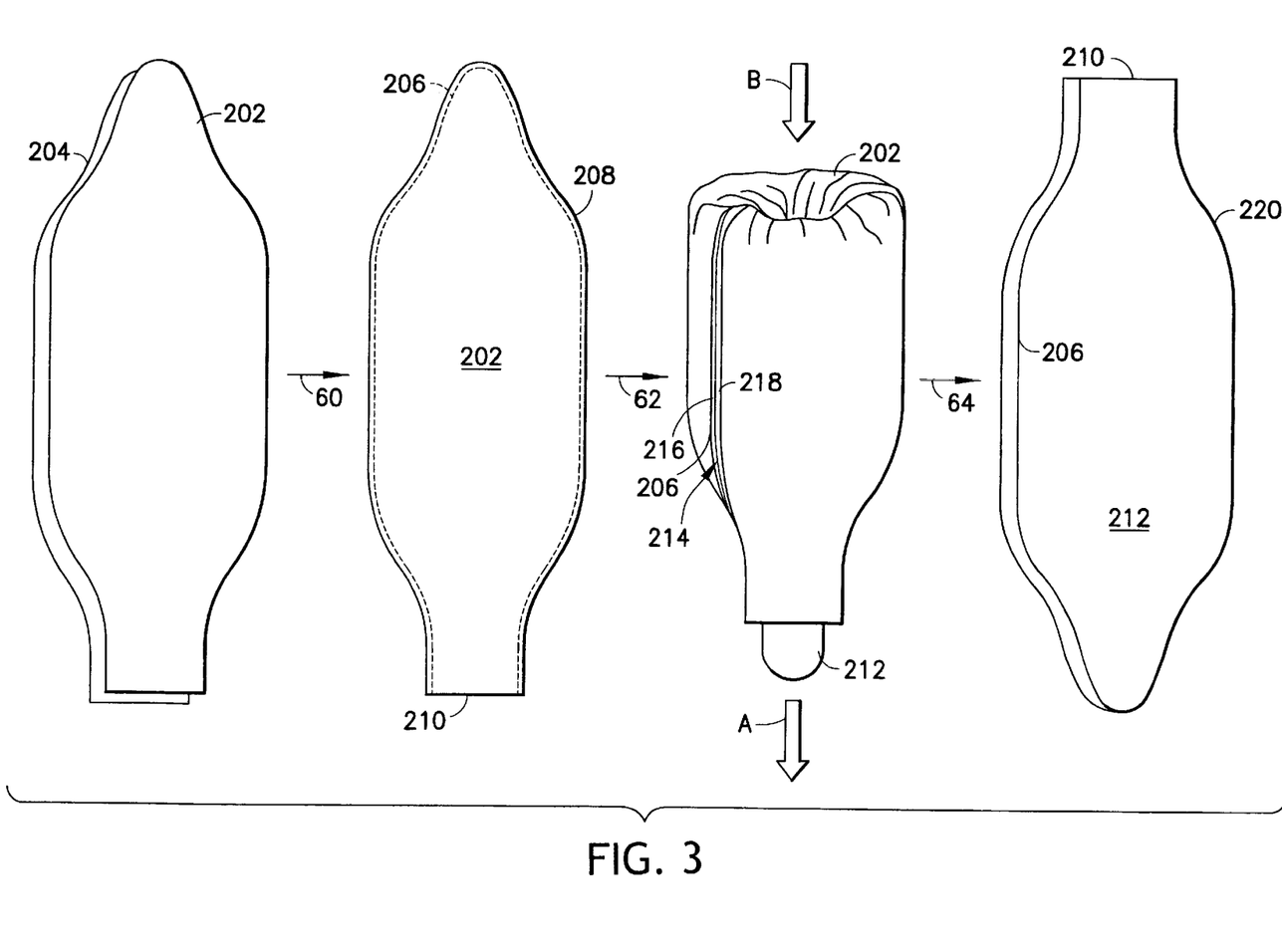
FIG. 3 is a schematic representation of a sequence of process steps for making a bag in accordance with a further aspect of the invention.

FIG. 3 is a schematic representation of a sequence of process steps for making a bag in accordance with a further aspect of the invention.

As illustrated in FIG. 3, the fabrication of the bag begins with the superpositioning of two sheets 202 and 204 of resin film material, preferably cut to the desired shape of the bag to be formed. After superpositioning of the sheets 202 and 204 (step one), the next step (progression indicated by arrow 60) is welding of the two sheets at their registered edge regions to form a weld line 206, producing outside edges 208 of the welded article (outside edge portions of the respective sheets 202 and 204, exterior to the weld line 206). The welding is carried out by suitable welding technique such as RF welding, heat impulse welding, solvent welding, adhesive bonding, etc., with RF welding generally being most preferred.

The welding (step two) produces a welded article with a proximal opening 210 which together with the weld line 206 bounds the interior volume of the welded article as shown in the step two structure.

From step two (progression indicated by arrow 62), the welded article is inverted as shown (step three). The exterior surface of sheet 202 of the step two article is interiorly disposed by drawing the distal end 212 of the welded article through the proximal opening 210 of the welded article, in the direction indicated by arrows A and B. In this manner, the seam structure 214 comprising weld line 206 and free edges 216 and 218, which formerly in step two was exteriorly disposed, is placed into the interior of the inverted article, so that the former exterior surface of constituent sheet 202 is thereby interiorly disposed together with such seam structure 214.

Next (progression being indicated by arrow 64, to final step 4), the fully inverted bag 220 has an exterior surface 212 that was previously an interior surface after the welding in step two. The bag has a smooth weld line 206. Open proximal end 210, by virtue of the inversion of the welded article, is oppositely presented at the top of the article in the position shown in step four, relative to the bottom presentation of such proximal opening shown in step two.

The final bag article shown in step four of FIG. 3 can be further finished by joining the open proximal end 210 to a collar structure of the type illustratively shown in FIG. 2A, or by other finishing steps, e.g., imparting a matte finish to the exterior surface of the bag if the constituent sheets 202 and 204 were not correspondingly matte finished as originally supplied, or applying a low-tack medium to the exterior surface of the bag for the same purpose (to enhance handleability and grippability, etc.).

The breathing bag of the present invention achieves a significant advance in the art by enabling the fabrication of seam-welded non-latex bags that thereby avoid the issues presented by latex exposure and sensitivity in hospital and healthcare environments.

Although the invention has been variously disclosed herein with reference to illustrative aspects, embodiments and features, it will be appreciated that the aspects, embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. A pulmonarily sized bag formed of a polyurethane material having a durometer not exceeding about 90 A, comprising a bag body formed of panels of polyurethane film material welded to one another along a weld line defining a seam of the bag body bounding an interior volume of the bag, wherein:
    (a) the seam comprises an interior seam portion in the interior volume, and an exterior seam portion at an exterior surface of the bag,
    (b) one of the interior seam portion and exterior seam portion comprises free edges of the seam, and the other of the interior seam portion and the exterior seam portion is devoid of free edges; and
    (c) the bag body has an elongate character, with an enlarged intermediate section relative to proximal neck and distal end portions of the bag body, wherein the proximal neck portion terminates at an open proximal end of the bag and the distal end portion terminates at a closed distal end of the bag, and the seam is continuous from the neck portion around the enlarged intermediate section and distal end portion of the bag.

2. The bag of claim 1, wherein the interior seam portion comprises free edges of the seam.

3. The bag of claim 1, wherein the exterior seam portion comprises free edges of the seam.

4. The bag of claim 1, wherein the interior volume is from about 0.5 liter to about 5 liters.

5. The bag of claim 1, wherein the interior volume is from about 0.75 liter to about 4 liters.

6. The bag of claim 1, wherein the interior volume is from about 1 liter to about 3 liters.

7. The bag of claim 1, wherein the modulus of elasticity at 50% elongation of the polyurethane film material is from about 50 to about 1500 psi.

8. The bag of claim 1, wherein the polyurethane film material has a durometer value of from about 10 A to about 98 A.

9. The bag of claim 1, wherein the polyurethane film material comprises blown film.

10. The bag of claim 1, wherein the polyurethane film material comprises extruded sheet.

11. The bag of claim 1, wherein the polyurethane film material comprises solvent cast film.

12. The bag of claim 1, wherein the panels of polyurethane film material have a thickness in the range of from about 1 to about 25 mils.

13. The bag of claim 1, wherein the panels of polyurethane film material have a thickness in the range of about 1 to about 10 mils.

14. The bag of claim 1, wherein the panels of polyurethane film material have a thickness in the range of from about 2 to about 6 mils.

15. The bag of claim 1, further comprising a collar joined to the neck portion of the bag body.

16. The bag of claim 15, wherein the collar is joined to the sheets of the bag during welding.

17. A pulmonarily sized bag formed of a non-latex material, comprising a bag body formed of panels of non-latex resin film material welded to one another along a weld line defining a seam of the bag body bounding an interior volume of the bag, wherein the seam comprises an interior seam portion in the interior volume, an an exterior seam portion at an exterior surface of the bag, wherein one of the interior seam portion and exterior seam portion comprises free edges of the seam, while the other of the interior seam portion and the exterior seam portion at the exterior surface of the bag is devoid of free edges, and wherein the panels of resin film material on an exterior surface of the bag body comprise a matte finish.

18. The bag of claim 1, wherein the polyurethane film material comprises a conductive material.

19. The bag of claim 1, wherein the polyurethane film material comprises at least one material selected from the group consisting of colored materials, pigment materials and filler materials.

20. The bag of claim 1, wherein the polyurethane film material comprises at least one material selected from the group consisting of surface modifiers, antioxidizers, heat stabilizers, and ultraviolet stabilizers.

21. The bag of claim 1, wherein the polyurethane film material comprises a flame retardant filler.

22. The bag of claim 1, wherein the seam strength of the bag is at least about 1000 pounds per square inch (psi).

23. The bag of claim 1, wherein the seam strength of the bag is at least about 30% of the strength of the unwelded panels.

24. The bag of claim 1, having a minimum seam dimension between the welded panels that is at least twice the thickness of the panels.

25. The bag of claim 1, having a maximum seam dimension between the welded panels of about 0.5 inch.

26. The bag of claim 1, having a seam dimension between the welded panels of from about 0.020 to about 0.050 inch.

27. The bag of claim 1, wherein the body portion of the bag has a circular, oval, dumbbell, or S-shape.

28. The bag of claim 17, wherein the panels of resin film material on an interior surface of the bag body comprise a smooth finish.

29. A pulmonarily sized bag formed of a polyurethane material having a durometer not exceeding about 90 A, comprising a bag body formed of panels of polyurethane film material welded to one another along a weld line defining a seam of the bag body bounding an interior volume of the bag, wherein:

(a) the seam comprises an interior seam portion in the interior volume, and an exterior seam portion at an exterior surface of the bag, (b) one of the interior seam portion and exterior seam portion comprises free edges of the seam, and the other of the interior seam portion and the exterior seam portion is devoid of free edges; and (c) the bag body has an elongate character, with an enlarged intermediate section relative to proximal neck and distal end portions of the bag body, wherein the proximal neck portion terminates at an open proximal end of the bag and the distal end portion terminates at a closed distal end of the bag, and the seam is continuous from the neck portion around the enlarged intermediate section and distal end portion of the bag;

(d) the modulus of elasticity at 50% elongation of the polyurethane film material is from about 50 to about 1500 psi (e) the polyurethane film material has a durometer value of from about 10 A to about 98 A;

(f) the seam strength of the bag is at least about 1000 pounds per square inch (psi) or is at least about 30% of the strength of unwelded panels;

(g) the panels of polyurethane film material have a thickness in the range of from about 1 to about 25 mils; and (h) the interior volume of the bag is from about 0.5 to about 5 liters.

\* \* \* \* \*

UNITED STATES PATENT AND TRADEMARK OFFICE
CERTIFICATE OF CORRECTION

PATENT NO.   : 6,352,077 B1
DATED        : March 5, 2002
INVENTOR(S)  : Tilak M. Shah It is certified that error appears in the above-identified patent and that said Letters Patent is hereby corrected as shown below:

<u>Column 8,</u>
Line 44, "sheets" should read -- panels --

Signed and Sealed this

Second Day of July, 2002

Attest:

JAMES E. ROGAN
Attesting Officer            Director of the United States Patent and Trademark Office